United States Patent [19]

Royston

[11] 4,006,349
[45] Feb. 1, 1977

[54] MONITORING APPARATUS FOR A PNEUMATIC CONVEYOR SYSTEM

[75] Inventor: Mark William Royston, La Mirada, Calif.

[73] Assignee: Pacific Pneumatics, Inc., Santa Fe Springs, Calif.

[22] Filed: Oct. 23, 1975

[21] Appl. No.: 625,266

[52] U.S. Cl. .............................. 235/151.34; 73/28; 73/37

[51] Int. Cl.² ................... G01N 15/06; G06F 15/20

[58] Field of Search ........... 235/151.34; 73/23, 28, 73/37, 194 E, 194 M, 388 R, 391

[56] References Cited

UNITED STATES PATENTS

| | | | |
|---|---|---|---|
| 3,315,524 | 4/1967 | Duffy et al. | 73/194 M |
| 3,408,866 | 11/1968 | Gibson et al. | 73/28 X |
| 3,545,674 | 12/1970 | Hanbicki | 73/37 X |
| 3,729,995 | 5/1973 | Kovacs et al. | 235/151.34 X |
| 3,744,297 | 7/1973 | Hanson et al. | 73/28 |
| 3,822,582 | 7/1974 | Etkin | 73/28 |

*Primary Examiner*—Jerry Smith
*Attorney, Agent, or Firm*—Christie, Parker & Hale

[57] ABSTRACT

A monitoring system measures the flow of solids in a pneumatic conveying system having a conduit with an air inlet, a solids inlet, and a mixture outlet. A pressure transducer responds to pressure in the conduit to produce a pressure-representing signal. Prior to the introduction of solids into the conduit and while only air flows through the conduit, the pressure-representing signal is sampled to provide a signal which is stored. After solids are introduced into the conduit, the pressure-representing signal is sampled again, preferably on a repetitious basis, and supplied to apparatus such as a computer which determines the difference between the pressure of air plus solids and the pressure of air, and multiplies this difference by a constant to determine the mass flow of solids.

5 Claims, 3 Drawing Figures

4,006,349

MONITORING APPARATUS FOR A PNEUMATIC CONVEYOR SYSTEM

BACKGROUND OF THE INVENTION

This invention relates to a monitoring system for a pneumatic conveying system.

Pneumatic conveying systems are widely used for transporting material (usually free-flowing) through conduits such as pipe or tubing. They may be used to transport material from truck or rail car or into storage, from storage to process, process to process, from process to storage, from process to truck or rail car, and from storage to truck or rail car. Many different types of systems are used, depending on the logistics of the application. The different types include vacuum driven systems, pressure driven systems, or combination vacuum/pressure systems. An air moving source, a conduit, an air inlet, a solids inlet, and a mixture outlet, are found in each type.

It is often necessary or desirable to provide a scaing system for the pneumatic conveying system. One type of scaling system employs a beam scale. In this type of scaling system, material is deposited into a hopper and weighed by a conventional beam scale. Another type of scaling system employs a belt scale, whereby material is passed over a belt with the speed of the belt and the deflection of the belt being measured, and the results calculated to determine the conveying rate and total material conveyed. In another known scaling system, the entire storage is placed on load cells, whereby the amount of material added to or subtracted from the storage results in a measureable displacement of the load cell. High and low level switches start and stop the transfer action automatically, or an operator watching the scale can start and stop the system as needed.

All of the above-described known scaling systems have disadvantages. In particular, these known scaling systems are expensive, require a considerable amount of space, involve dirt and dust problems, and require extensive maintenance.

SUMMARY OF THE INVENTION

This invention is directed to a system for measuring the flow of solids in a pneumatic conveying system having a conduit with an air inlet, a solids inlet, and a mixture outlet. Briefly, the measuring system comprises transducer means coupled to the conduit for producing a pressure-representing signal, and means responsive to the pressure-representing signal for determining the mass flow of solids on the basis of a linear function of the pressure-representing signal.

In a preferred embodiment, means are provided for sequentially sampling the pressure-representing signal to provide a reference-value representing signal and an operating-value-representing signal. The sampling means provides the reference-value-representing signal when only air flows through the conduit, and provides the operating-value-representing signal at a time when both air and solids flow through the conduit. The linear function is defined by first and second terms. The first term is proportional to the difference between the operating value and reference value and the second term is given by the reciprocal of the reference-value. Manually adjustable means are provided for specifying a constant proportionally for proportionality first term. The measuring system preferably comprises means for accumulating a total to designate the amount of solids conveyed by the conveying system. To this end, the sampling means provides for repetitiously sampling the pressure-representing signal so that the operating-value-signal repeatedly provides information as to instantaneous pressure.

DETAILED DESCRIPTION

Figure 1:
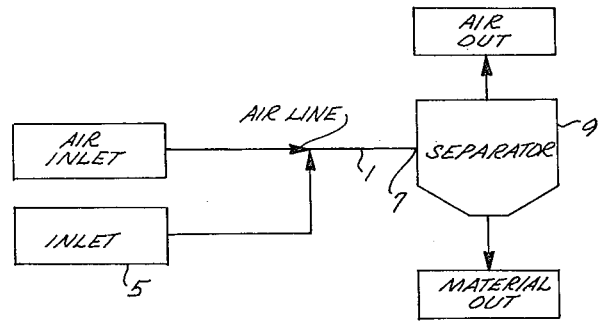
FIG. 1 is a block diagram of an exemplary pneumatic conveying system for which the monitoring system of this invention is adapted to measure the flow of solids.

With reference to FIG. 1, a pneumatic conveying system depicted therein includes a conduit 1 having an air inlet 3, a solids inlet 5, and a mixture outlet 7. A separator such as cyclone 9 is connected to the mixture outlet, and operates to separate the solids from the air. Such pneumatic conveying systems are well known and can be used for conveying a wide variety of different types of solids either on a vacuum-drive basis or on a pressure-drive basis.

In conventional practice, there is an initial stage of operation in which only air flows through the pneumatic conveying system. During this initial stage, various operating parameters are stabilized. Then solids are introduced into the solids inlet whereby a mixture of air plus solids flows through the pneumatic conveying system.

With solids flowing through the pneumatic conveying system, the total pressure drop between any two arbitrary points in the system (referred to herein as $P_T$) is higher than the pressure drop between these points when only air flows (referred to herein as $P_1$). It has been discovered that a determination of the flow of solids can be effected on a basis of a linear function of $P_T$. A particularly accurate determination can be effected through evaluation of the following function:

$$Qm = KQ_a \left[ \frac{P_T - P_a}{P_a} \right]$$

where
$Qm$ = Quantity (or rate) of solids being conveyed expressed in units consistent with $Q_1$;
$Q_a$ = Quantity (or rate) of conveying air passing through the conduit;
$K$ = A constant having a predetermined value for each particular pneumatic conveying system.

Figure 2:
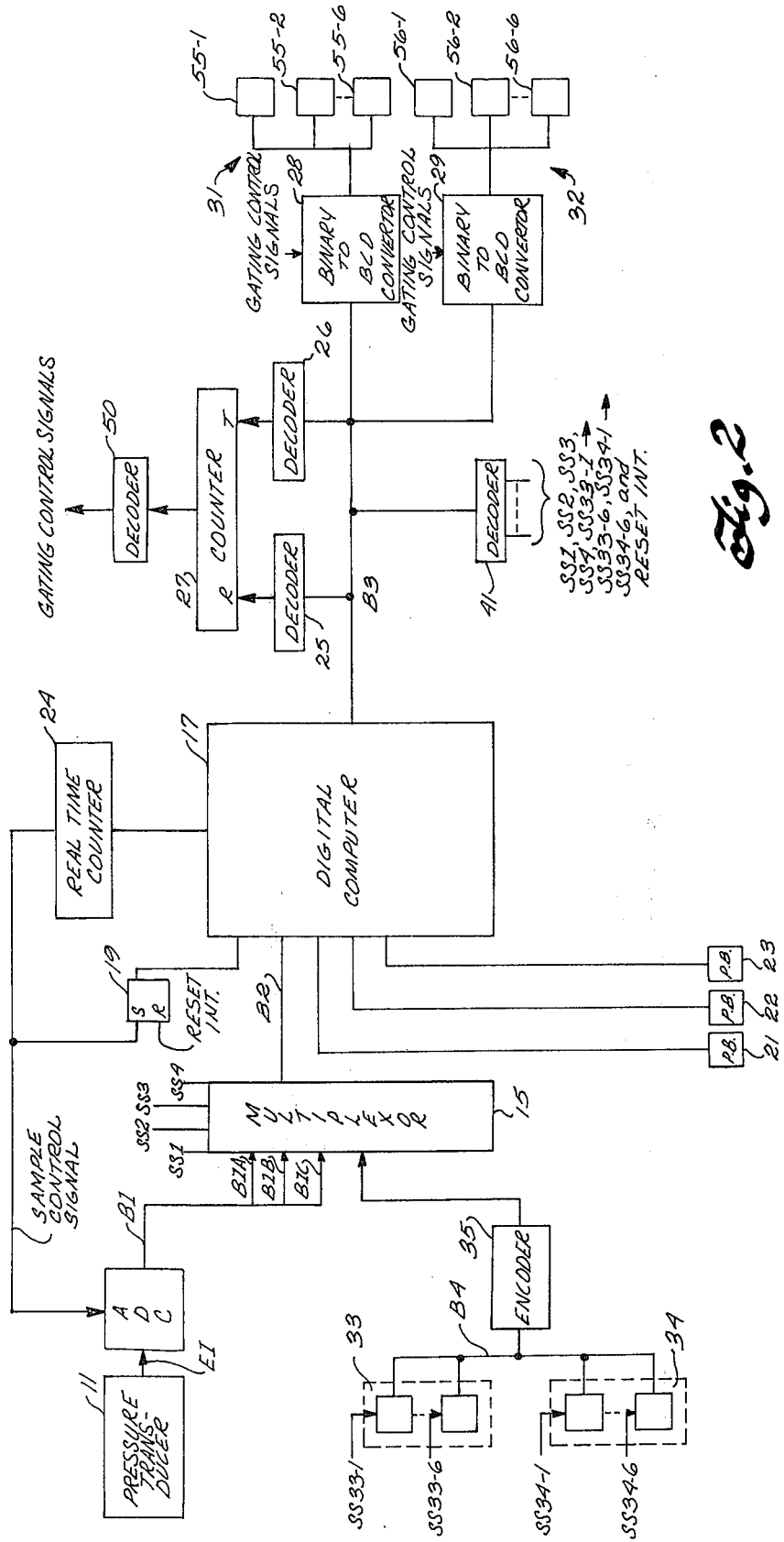
FIG. 2 is a block diagram of a specific embodiment of the monitoring system of this invention.

With reference to FIG. 2, there will now be described the general organization of a specific embodiment of the monitoring system of this invention.

A pressure transducer 11 is coupled to the conduit 1, and provides a pressure-representing signal EI in the form of an analog signal. The manufacturer of the transducer used in this specific embodiment is Viatran Corporation, Grand Island, New York. One way in which the pressure transducer can be coupled to the conduit is by a single tube whereby the transducer measures gage pressure defined at the point in the pneumatic conveying system where the tube is connected. In this way, the pressure-representing signal represents the drop in pressure between that point and a discharge point. Another way of coupling involves two tubes coupled to spaced-apart points whereby the transducer responds to the difference in pressure between the two points.

A conventional analog-digital converter (ADC 13) has an analog-signal input connected to receive the pressure-representing signal EI, a control-signal input connected to receive a sample control signal, and an output connected to a bus B1 comprising twelve wires (not individually shown). The ADC 13 used in this specific embodiment is commercially available under the designation DATEL ADC-K 12 B. The ADC 13 applies to the bus a sampled signal in the form of a 12 bit wide binary number. This binary number is made up of three fields, each being four bits wide, that are carried by three sub buses B1A, B1B, and B1C of the bus B1.

A conventional multiplexor 15 is provided for selectively coupling four bit wide data signals to a bus B2 comprising four wires (not individually shown). A digital computer 17 is connected to the bus B2. The digital computer used in this specific embodiment is manufactured by Pro-Log Corporation under the designation PLS-400. It has eigh input terminals for receiving input data, and eight output terminals for providing output data and control signals. Four of the input terminals, referred to herein as DTIN 1, DTIN 2, DTIN 4, and DTIN 8, are connected to the four wires of the bus B2. The other four input terminals, referred to herein as DTIN 16, DTIN 32, DTIN 64, and DTIN 128, are connected to receive binary valued signals produced by a flip-flop 19, and by push buttons 21, 22, and 23.

Within the digital computer 17, there is a clock pulse source (not separately shown) whose output is applied to a real time counter 24. The output of the counter 24 is a pulse train having a pulse repetition frequency of 1024 pulses per hour, and is applied to the ADC 13 as the sample control signal.

The eight output terminals of the digital computer 17 are connected to a bus B3 comprising eight wires (not individually shown). These eight output terminals are referred to herein as OPD 1, OPD 2, OPD 4, OPD 8, OPD 16, OPD 32, OPD 64, and OPD 128. A decoder 25 and a decoder 26 are provided for decoding fields of digital words carried by the bus B3. The decoder 25 is operative to reset a control counter 27 and the decoder 26 is operative to trigger the control counter 27 so that it counts up.

The bus B3 is also connected to two parallel binary-BCD converters 28 and 29 that form parts of display apparatus indicated generally at 31 and 32.

Figure 3:
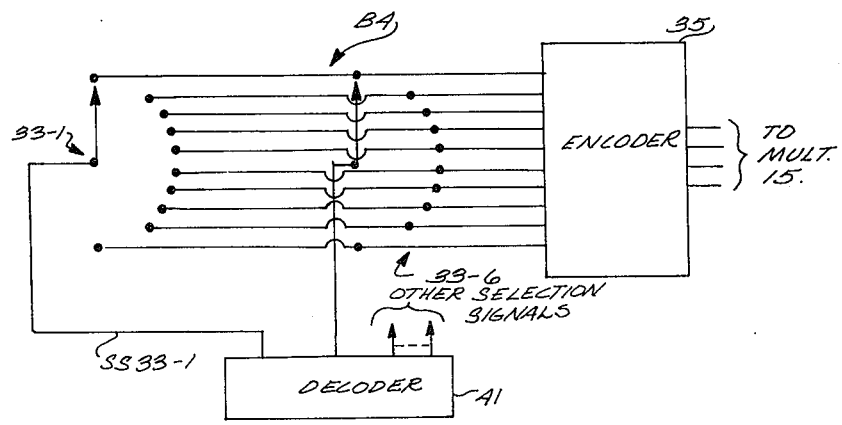
FIG. 3 is a block and schematic diagram depicting in more detail an arrangement of elements of the system of FIG. 2 which are involved in specifying a constant-representing signal.

In addition to information provided by the transducer 11, the digital computer 17 also receives information defined by manually adjustable means 33 for producing a constant-representing signal. In this specific embodiment, there are provided six digi-switches 33-1 through 33-6 (not all depicted). The digi-switches can be manually set to represent an arbitrary decimal constant within the range between 00000.0 through 99999.9. The setting of each digi-switch designates a decimal coefficient, with digi-switch 33-1 designating th coefficient for $10^{-1}$, digi-switch 33-2 designating the coefficient for $10^0$, and so forth such that digi-switch 33-6 designates the coefficient for 10. A bus B4 comprising ten wires (individually shown in FIG. 3) connects the digi-switches to an encoder 35. Digital data determined by the manual setting of the digi-switches is in the form of a one out of ten code. The encoder 35 responds to this type of code to provide a 4 bit-wide binary coded decimal code to the multiplexor 15.

A feature of this specific embodiment resides in a batch mode of operation. This mode of operation is useful in circumstances wherein it is desirable for the pneumatic conveying system to convey a specified amount of solids. To this end, there is provided manually adjustable means 34 for producing a total-amount representing signal. In this specific embodiment, there are provided six digi-switches 34-1 through 34-6 (not all depicted). The bus B4 connects these digi-switches to the encoder 35 by virtue of connections identified to those illustrated by way of example in FIG. 3.

Within the digital computer 17 there are provided three programmable read only memories (PROMs). The PROMs store a program executed by the digital computer 17. A complete listing of this program is provided in a Table given at the end of this specification. Through execution of instructions in this listing, the digital computer 17 determines the flow of solids on the basis of a linear function.

As to the overall operation of the system, the following points bear mention here. The optimum constant of proportionality for the linear function will vary from one pneumatic control system to another, depending upon such factors as pipe diameter, and the like. It is therefore advisable to optimize the selection of this constant of proportionality when the monitoring system is first used with a particular pneumatic conveying system. To do this, a known amount of solids is conveyed. With an arbitrarily selected constant of proportionality inputted into the monitoring system, the computed results can be compared against the known amount. If the computer results are correct, than the arbitrarily selected constant proportionality is already optimized. If not, a new constant is selected on the basis of the ratio between the computer results and the known amount.

As has been previously stated, it is conventional practice for a pneumatic conveying system to have an initial stage of operation whereby only air flows. The push button 21, referred to herein as a calibrate push button, is manually depressed and automatically held latched during this initial stage of operation. The digital computer 17 will respond to the signal by the button 21 to execute instructions causing read-in of information as to the pressure-representing signal. The instructions relating to this are shown bracketed next to the comment "Receive $P_1$ Save". Inasmuch as a 12 bit wide number is defined by the output of the ADC 13 and the bus B2 carries only 4 bits at a time, three sub fields are inputted in a sequential manner in response to commands produced by the computer. To alert the other elements of the system that the computer is ready to accept input data, the computer first provides a read-in control command. To select the first field of 4 bits from the 12 bit wide number, the computer provides a binary 1 on an output terminal OPD 64 and simultaneously provides binary zeros on each of the following outputs, OPD 32, OPD 16, OPD 8, and OPD 4. A decoder 41 detects this code and provides a selection signal SS1 causing the multiplexor 15 to gate the first field to the computer 17. The second and third fields are similarly selected. The output codes for commanding these fields to be read are as follows. For the second field, OPD 64 and OPD 4 each equal one, and OPD 32, OPD 16, and OPD 8 each equal 0, and decoder 41 provides an S2 selection signal. For the third field, OPD 64 and OPD 8 each equal 1; and OPD 32, OPD 16 and OPD 4 each equal 0, and decoder 41 provides an S3 selection signal.

The following Table provides a list of the foregoing read-in control commands and additionally list similar read-in control commands involved in commanding the read-in of data as to the constant-representing signal (from digital switches 33) and as to the batch signal (from digi-switches 34).

OPD 128, and OPD 64 equals 1, and OPD 32 equals 0. The decoder 26 detects this code in the identification field, and triggers the counter. The state of the counter 27 is decoded by decoder 50 to provide gating signals which are applied to the converters 28 and 29.

Each of these converters comprises a conventional arrangement for receiving and storing in sequence fields that when concatenated define a binary number, and for converting this binary number to a binary coded decimal number. Such a conventional arrangement (not shown in detail) includes a binary down

TABLE

| COMPUTER OUTPUT COMMAND | | | | | DECODER 41 SELECTION SIGNAL | BUS B2 CARRIES | |
|---|---|---|---|---|---|---|---|
| OPD 64 | OPD 32 | OPD 4 | OPD 8 | OPD 16 | | | |
| 0 | 0 | 0 | 0 | 0 | SS4 & SS33-1 | $10^{-1}$ | coefficient |
| 0 | 0 | 1 | 0 | 0 | SS4 & SS33-2 | $10^0$ | " |
| 0 | 0 | 0 | 1 | 0 | SS4 & SS33-3 | $10^1$ | " |
| 0 | 0 | 1 | 1 | 0 | SS4 & SS33-4 | $10^2$ | " |
| 0 | 0 | 0 | 0 | 1 | SS4 & SS33-5 | $10^3$ | " |
| 0 | 0 | 1 | 0 | 1 | SS4 & SS33-6 | $10^1$ | " |
| 0 | 1 | 0 | 0 | 0 | SS4 & SS34-1 | $10^0$ | " |
| 0 | 1 | 1 | 0 | 0 | SS4 & SS34-2 | $10^1$ | " |
| 0 | 1 | 0 | 1 | 0 | SS4 & SS34-3 | $10^2$ | " |
| 0 | 1 | 1 | 1 | 0 | SS4 & SS34-4 | $10^3$ | " |
| 0 | 1 | 0 | 0 | 1 | SS4 & SS34-5 | $10^4$ | " |
| 0 | 1 | 0 | 1 | 1 | SS4 & SS34-6 | $10^5$ | " |
| 1 | 0 | 0 | 0 | 0 | SS1 | B1A | subfield |
| 1 | 0 | 1 | 0 | 0 | SS2 | B1B | " |
| 1 | 0 | 0 | 1 | 0 | SS3 | B1C | " |

The decoder 41 also detects another code and in response provides a Reset Interrupt Command signal used to reset reset flip-flop 19. This code is such that OPD 128 and OPD 32 each equal 1, and OPD 64 equals 0. The flip-flop 19 is set by the pulses of the sample signal. Thus, every 1/1024th of an hour, the flip-flop 19 is set and its output defines a binary 1 for the purpose of interrupting the computer. Upon being interrupted, the computer provides the read-in commands and then provides the code which causes flip-flop 19 to reset.

While the calibrate pushbutton 21 is latched, the pressure-representing signal provides information on a sampled basis as to the instantaneous pressure, and the computer operates in a calibrate mode. The computer then provides, in a manner described in more detail hereinafter, computed results as to the extent to which the instantaneous pressure has approached a stabilized or full scale reading. It will be recalled that at this stage of operation, the instantaneous pressure designates the variable $P_a$ of the linear function.

When stabilized operating conditions are achieved, then the pushbutton 22 is manually depressed and automatically latched. This pushbutton is referred to herein as the Run pushbutton. At this point, the computer ceases operating in its calibrate mode and begins operating in a run mode. Thereafter, the previously computed results as to $P_a$ are stored in the digital computer and used in determining the computed results as to Qm.

Consider now further the outputting of data from computer 17. The format of the output data is such that 4 bit wide data words are provided on the output terminals OPD 8, OPD 16, OPD 32, and OPD 64. Prior to outputting the data words, a command output is first defined whereby OPD 128, OPD 64, and OPD 32 each equal 1. The decoder 25 detects this code and resets the control counter 27. Thereafter, data words are outputted along with an identification field whereby counter; means responsive to the gating control signals for sequentially loading four bit wide groups of flip-flops in the binary counter, and an up counter arranged to count in BCD. Thus, as the gating signals are produced by the decoder 50, four bit wide data words from the computer output are loaded sequentially into successive groups of flip-flops in the binary counter until the binary counter is filled and defines a binary number. At this point, both the binary down counter and the BCD up counter become responsive to a clock pulse train. The binary downcounter will thus count down until it reaches binary 0, and the BCD counter will count up until it stores a BCD number equal to the binary number that was loaded into the binary downcounter. Digit display elements 55-1 through 55-6 and 56-2 through 56-6 are responsive to the respective decimal-digit defining signal provided by the BCD counters.

The group of display elements 55 are used in a calibrate mode to display the computed percentage of full scale of the sampled pressure-representing signal. Thus, an operator viewing this display can recognize when the pneumatic conveying system has achieved stabilized initial operating conditions. At this point, the operator presses the run pushbutton. Thereafter (in the run mode), the group of display elements 55 is used to display the cumulative number of pounds conveyed, as computed by the digital computer 17. The group of display elements 56 are used to display the computed value of conveying rate. To provide for preserving certain computed results in the event of a disturbance in the pneumatic conveying system involving surging, blocking of flow and the like, the computer is responsive to the pushbutton 23 to be placed in a hold mode.

It will be appreciated from the foregoing that the monitoring system of FIG. 2 provides a transducer coupled to the conduit for providing a pressure representing signal, and means responsive to the pressure representing signal for determining the mass flow of solids on the basis of a linear function of the pressure representing signal. Preferably th signal responsive means includes a digital computer that is operable in a calibrate mode and in a run mode. During the run mode, storage means in the digital computer hold a reference-value-representing signal that is provided to the storage means as a result of the operation of the computer in the calibrate mode. In particular, the ADC 13 serves to sample the pressure representing signal for providing the reference value signal to the storage means at a time when only air flows through the conduit. In the run mode the sampling means resamples the pressure representing signal at a time when both air and solids flow through the conduit to provide an operating-value representing signal. The digital computer, through execution of the instructions listed in the Table given below, evaluates a linear function defined by the ratio of first and second terms. The first term equals the product of a constant proportionality and the difference between the operating value and the reference value. The second term equals the reciprocal of the reference value.

Preferably, the digital computer, through execution of the listed instructions, accumulates a total to designate the amount of solids conveyed by the conveying system. This running total is compared with stored information as to the batch desired. For this, see the instructions at addresses φ42-φ45 of PROM 1. When the running total equals the batch number, a signal is provided which can be used to close a relay or the like for stopping further conveying.

It will be evident that those skilled in this art that analog computer equipment can perform the same function as the digital computer 17 as programmed by the program listing given below.

TABLE GIVING PROGRAM LIST

| Address | | Instruction | | Comments |
|---|---|---|---|---|
| PROM 0 | 000 | NOOP | 00 | |
| | 1 | NOOP | 00 | |
| | 2 | LDM | D0 | Set R, 0, 1 = O |
| | 3 | XCH | B0 | Set 2, 3 = 1 |
| | 4 | LDM | D1 | For I/O SRC |
| | 5 | XCH | B2 | |
| | 6 | JMS | 50 | Clear IB |
| | 7 | | 66 | |
| | 8 | FIM | 24 | |
| | 9 | | 20 | |
| | A | JMS | 50 | Move IB to AUX |
| | B | | 6E | |
| | C | JMS | 50 | Output Routine |
| | D | | B2 | |
| | E | SRC | 23 | Input PB/INT |
| | F | RDR | EA | |
| | 010 | RAR | F6 | Test CAL PB |
| | 1 | JCN | 12 | |
| | 2 | | 15 | |
| | 3 | JUN | 40 | Retry |
| | 4 | | 0E | |
| | 5 | SCR | 23 | |
| | 6 | RDR | EA | |
| | 7 | RAL | F5 | Interrupt |
| | 8 | JCN | 12 | |
| | 9 | | 1c | |
| | A | JUN | 40 | |
| | B | | 15 | |

TABLE GIVING PROGRAM LIST (continued)

| Address | | Instruction | | Comments |
|---|---|---|---|---|
| PROM 0 | C | JMS | 50 | ACK Int |
| | D | | C8 | |
| | E | FIM | 28 | |
| | F | | 10 | Binary IN to R1 0 − 7 [receive P_n and save] |
| | 020 | JMS | 50 | |
| | 1 | | F7 | |
| | 2 | JMS | 50 | Clear IB |
| | 3 | | 66 | |
| | 4 | FIM | 24 | |
| | 5 | | 18 | Move IB to ACC Total |
| | 6 | JMS | 50 | |
| | 7 | | 6E | |
| | 8 | FIM | 24 | |
| | 9 | | 10 | Move R1 0 − 7 to IB |
| | A | JMS | 50 | |
| | B | | 78 | |
| | C | JMS | 50 | IB × 10 |
| | D | | 95 | |
| | E | JMS | 50 | IB × 10 |
| | F | | 95 | |
| | 030 | LDM | D5 | |
| | 1 | XCH | BA | |
| | 2 | JMS | 50 | RS IB |
| | 3 | | 56 | |
| | 4 | LDM | DC | |
| | 5 | XCH | BA | LS IB |
| | 6 | JMS | 50 | |
| | 7 | | 4A | |
| PROM 0 | 8 | FIM | 24 | |
| | 9 | | 20 | IB to AUX |
| | A | JMS | 50 | |
| | B | | 6E | |
| | C | JMS | 50 | Clear IB |
| | D | | 66 | |
| | E | JMS | 50 | Out |
| | F | | B2 | |
| | 040 | SRC | 23 | |
| | 1 | RDR | EA | |
| | 2 | RAR | F6 | |
| | 3 | RAR | F6 | |
| | 4 | JCN | 12 | RUN |
| | 5 | | 48 | |
| | 6 | JUN | 40 | |
| | 7 | | 15 | |
| | 8 | JUN | 41 | |
| | 9 | | 00 | |
| | A | FIM | 26 | |
| | B | | 28 | |
| | C | CLC | F1 | |
| | D | SRC | 27 | |
| | E | RDM | E9 | |
| | F | RAL | F5 | LEFT SHIFT IB |
| | 050 | WRM | E0 | |
| | 1 | ISZ | 77 | |
| | 2 | | 4D | |
| | 3 | ISZ | 7A | |
| | 4 | | 4A | |
| | 5 | BBL | C0 | |
| PROM 0 | 6 | FIM | 26 | |
| | 7 | | 2F | |
| | 8 | LDM | D8 | |
| | 9 | XCH | BB | |
| | A | CLC | F1 | |
| | B | SRC | 27 | |
| | C | RDM | E9 | |

-continued

TABLE GIVING PROGRAM LIST

| Address | | Instruction | | Comments |
|---|---|---|---|---|
| | D | RAR | F6 | Right Shift IB |
| | E | WRM | E0 | |
| | F | RAL | F5 | |
| 060 | | XCH | B7 | |
| | 1 | DAC | F8 | |
| | 2 | XCH | B7 | |
| | 3 | RAR | F6 | |
| | 4 | JUN | 40 | |
| | 5 | | D0 | |
| | 6 | FIM | 26 | Clear IB |
| | 7 | | 28 | |
| | 8 | LDM | D0 | |
| | 9 | SRC | 27 | |
| | A | WRM | E0 | |
| | B | ISZ | 77 | |
| | C | | 68 | |
| | D | BBL | C0 | |
| PROM 0 | E | FIM | 26 | IB to Memory |
| | F | | 28 | |
| 070 | | SRC | 27 | |
| | 1 | RDM | E9 | |
| | 2 | SRC | 25 | |
| | 3 | WRM | E0 | |
| | 4 | INC | 65 | |
| | 5 | ISZ | 77 | |
| | 6 | | 70 | |
| | 7 | BBL | C0 | |
| | 8 | FIM | 26 | Memory to IB |
| | 9 | | 28 | |
| | A | SRC | 25 | |
| | B | RDM | E9 | |
| | C | SRC | 27 | |
| | D | WRM | E0 | |
| | E | INC | 65 | |
| | F | ISZ | 77 | |
| 080 | | | 7A | |
| | 1 | BBL | C0 | |
| | 2 | FIM | 26 | Binary Input to R1, 0 – 7 |
| | 3 | | 28 | |
| | 4 | SRC | 23 | |
| | 5 | LD | A8 | |
| | 6 | WRR | E2 | |
| | 7 | LD | A9 | |
| | 8 | SRC | 21 | |
| | 9 | WRR | E2 | |
| | A | RDR | EA | |
| PROM 0 | B | SRC | 27 | Binary Input to R1, 0 – 7 |
| | C | WRM | E0 | |
| | D | INC | 69 | |
| | E | ISZ | 77 | |
| | F | | 84 | |
| 090 | | NOOP | | |
| | 1 | NOOP | | |
| | 2 | JMS | 50 | |
| | 3 | | 6E | |
| | 4 | BBL | C0 | |
| | 5 | | | |
| | 6 | | | |
| | 7 | | | |
| | 8 | | | |
| | 9 | | | |
| | A | | | |
| | B | | | |
| | C | | | |
| | D | | | |
| | E | | | |
| | F | | | |
| 0A0 | | | | |
| | 1 | | | |
| | 2 | | | |
| | 3 | | | |
| | 4 | | | |
| | 5 | | | |
| | 6 | FIM | 26 | |
| | 7 | | 28 | |
| PROM 0 | 8 | CLC | F1 | |
| | 9 | SRC | 25 | |

-continued

TABLE GIVING PROGRAM LIST

| Address | | Instruction | | Comments |
|---|---|---|---|---|
| | A | RDM | E9 | Memory Add to IB |
| | B | SRC | 27 | |
| | C | ADM | EB | |
| | D | WRM | E0 | |
| | E | INC | 65 | |
| | F | ISZ | 77 | |
| 0B0 | | | A9 | |
| | 1 | BBL | C0 | |
| | 2 | SRC | 23 | Output Routine |
| | 3 | LDM | D0 | |
| | 4 | WRR | E2 | |
| | 5 | LDM | DE | |
| | 6 | WRR | E2 | |
| | 7 | LDM | D0 | |
| | 8 | WRR | E2 | |
| | 9 | FIM | 26 | |
| | A | | 20 | |
| | B | SRC | 27 | |
| | C | RDM | E9 | |
| | D | SRC | 21 | |
| | E | WRR | E2 | |
| | F | SRC | 23 | |
| 0C0 | | LDM | DC | |
| | 1 | WRR | E2 | |
| | 2 | LDM | D0 | |
| | 3 | WRR | E2 | |
| | 4 | ISZ | 77 | |
| PROM 0 | 5 | | BB | |
| | 6 | BBL | C0 | |
| | 7 | NOOP | | |
| | 8 | LDM | D0 | Ack Int |
| | 9 | SRC | 23 | |
| | A | WRR | E2 | |
| | B | LDM | DA | |
| | C | WRR | E2 | |
| | D | LDM | D0 | |
| | E | WRR | E2 | |
| | F | BBL | C0 | |
| 0D0 | | ISZ | 7B | Part of Right Shift IB |
| | 1 | | 5B | |
| | 2 | ISZ | 7 | |
| | 3 | | 56 | |
| | 4 | BBL | C0 | |
| | 5 | JMS | 50 | Decimal Inputs |
| | 6 | | 66 | |
| | 7 | SRC | 23 | |
| | 8 | LDM | D8 | |
| | 9 | XCH | BE | |
| | A | LD | A8 | |
| | B | WRR | E2 | |
| | C | LD | A9 | |
| | D | SRC | 21 | |
| | E | WRR | E2 | |
| | F | RDR | EA | |
| 0E0 | | XCH | BF | |
| | 1 | CLB | F0 | |
| Prom 0 | 2 | JMS | 50 | IB × 10 |
| | 3 | | 95 | |
| | | JMS | 50 | IB + F → |
| | 4 | | EC | Part of Decimal Inputs |
| | 5 | LD | A9 | |
| | | DAC | F8 | |
| | | XCH | B9 | |
| | 6 | ISZ | 7E | |
| | 7 | | DC | |
| | 8 | BBL | C0 | |
| | 9 | | | |
| | A | | | |
| | B | | | |
| | C | CLB | F0 | |
| | D | XCH | BF | |
| | E | FIM | 26 | |
| | F | | 28 | |
| 0F0 | | SRC | 27 | |
| | 1 | ADM | EB | IB + F → IB |
| | 2 | WRM | E0 | |
| | 3 | LDM | D0 | |
| | 4 | ISZ | 77 | |
| | 5 | | F0 | |
| | 6 | BBL | C0 | |
| | 7 | FIM | 24 | |

-continued

TABLE GIVING PROGRAM LIST

| Address | | Instruction | | Comments |
|---|---|---|---|---|
| | 8 | | 10 | |
| | 9 | JUN | 40 | |
| | A | | 82 | |
| | B | FIM | 24 | |
| | C | | 30 | |
| | D | JUN | 40 | |
| | E | | 82 | |
| | F | NOOP | | |

TABLE GIVING PROGRAM LIST

| Address | | Instruction | | Comments |
|---|---|---|---|---|
| PROM 1 | 000 | SRC | 23 | |
| | 1 | RDR | EA | |
| | 2 | RAL | F5 | |
| | 3 | JCN | 12 | |
| | 4 | | 07 | |
| | 5 | JUN | 41 | |
| | 6 | | 00 | |
| | 7 | JMS | 50 | |
| | 8 | | C8 | |
| | 9 | FIM | 28 | |
| | A | | 07 | |
| | B | JMS | 50 | Rate In |
| | C | | D5 | (KQA) |
| | D | FIM | 24 | |
| | E | | 00 | |
| | F | JMS | 50 | |
| 010 | | | 6E | |
| | 1 | FIM | 28 | |
| | 2 | | 0F | |
| | 3 | JMS | 50 | |
| | 4 | | D5 | Batch In |
| | 5 | FIM | 24 | Total Batch Desired |
| | 6 | | 08 | |
| | 7 | JMS | 50 | |
| | 8 | | 6E | |
| | 9 | FIM | 28 | |
| | A | | 10 | PR→30  PT Input |
| | B | JMS | 50 | PR − P0 INIB PT − PA |
| PROM 1 | C | | FB | |
| | D | FIM | 24 | |
| | E | | 30 | |
| | F | JMS | 50 | |
| 020 | | | 78 | |
| | 1 | FIM | 24 | PR→30 |
| | 2 | | 10 | PR − P0 INIB |
| | 3 | JMS | 51 | |
| | 4 | | 90 | |
| | 5 | FIM | 24 | |
| | 6 | | 2F | |
| | 7 | SRC | 25 | Test for PR − P0 < 0 |
| | 8 | RDM | E9 | PT − PA < 0 |
| | 9 | RAL | F5 | |
| | A | JCN | 1A | |
| | B | | 2E | |
| | C | JMS | 50 | Zero Flow Rate |
| | D | | 66 | |
| | E | FIM | 24 | |
| | F | | 30 | PR − P0 → |
| 030 | | JMS | 50 | Save PT − PA |
| | 1 | | 6E | |
| | 2 | JMS | 52 | Divide R30 ÷ 10 × R10 →R30 |
| | 3 | | 40 | Compute $\frac{KQA}{PA}$ |
| | 4 | JMS | 52 | MPY R0$_0$ × R30 → R0$_0$ and IB |
| | 5 | | 00 | Compute $\frac{KQA}{PA}$ (PT − PA) |
| | 6 | | | |

TABLE GIVING PROGRAM LIST

| Address | | Instruction | | Comments |
|---|---|---|---|---|
| | 7 | | | |
| | 8 | | | |
| PROM 1 | 9 | | | |
| | A | | | |
| | B | | | |
| | C | | | |
| | D | | | Right Shift 10 |
| | E | LDM | D6 | |
| | F | XCH | BA | |
| 040 | | JMS | 50 | |
| | 1 | | 56 | |
| | 2 | FIM | 24 | |
| | 3 | | 08 | Subtract Batch No. |
| | 4 | JMS | 51 | Compare to Batch Desired |
| | 5 | | 90 | |
| | 6 | FIM | 24 | |
| | 7 | | 2F | |
| | 8 | SRC | 25 | |
| | 9 | RDM | E9 | |
| | A | RAL | F5 | |
| | B | JCN | 12 | |
| | C | | 51 | |
| | D | LDM | DF | |
| | E | XCH | BF | |
| | F | JUN | 41 | |
| 050 | | | 53 | |
| | 1 | LDM | D0 | |
| | 2 | XCH | BF | |
| | 3 | FIM | 24 | |
| | 4 | | 18 | |
| | 5 | JMS | 50 | |
| PROM 1 | 6 | | 78 | |
| | 7 | LDM | D6 | |
| | 8 | XCH | BA | |
| | 9 | JMS | 50 | |
| | A | | 56 | |
| | B | NOOP | | |
| | C | NOOP | | |
| | D | NOOP | | |
| | E | NOOP | | |
| | F | FIM | 24 | |
| 060 | | | 21 | |
| | 1 | JMS | 50 | |
| | 2 | | 6E | |
| | 3 | FIM | 24 | |
| | 4 | | 00 | |
| | 5 | JMS | 50 | |
| | 6 | | 78 | |
| | 7 | | | |
| | 8 | | | |
| | 9 | | | |
| | A | | | |
| | B | | | |
| | C | | | |
| | D | FIM | 24 | |
| | E | | 26 | |
| | F | JMS | 50 | |
| 070 | | | 6E | |
| | 1 | FIM | 24 | |
| | 2 | | 2F | |
| PROM 1 | 3 | SCH | BF | |
| | 4 | SRC | 25 | |
| | 5 | WRM | E0 | |
| | 6 | JMS | 50 | |
| | 7 | | B2 | |
| | 8 | SRC | 23 | |
| | 9 | | EA | |
| | A | | F6 | |
| | B | | F6 | |
| | C | | 12 | |
| | D | | 00 | |
| | E | | EA | |
| | F | | F6 | |
| PROM 1 | 080 | | 12 | |
| | 1 | | 84 | |
| | 2 | | 41 | |
| | 3 | | 78 | |
| | 4 | | 40 | |
| | 5 | | 00 | |
| | 6 | | | |
| | 7 | | | |
| | 8 | | | |
| | 9 | | | |
| | A | | | |
| | B | | | |
| | C | | | |
| | D | | | |

-continued

| Address | | Instruction | | Comments |
|---|---|---|---|---|
| | E | | | |
| | F | | | |
| PROM 1 | 090 | FIM | 26 | |
| | 1 | | 28 | |
| | 2 | CLC | F1 | |
| | 3 | SRC | 27 | |
| | 4 | RDM | E9 | |
| | 5 | SRC | 25 | |
| | 6 | SBM | E8 | |
| | 7 | SRC | 27 | |
| | 8 | WRM | E0 | |
| | 9 | CMC | F3 | |
| | A | INC | 65 | |
| | B | ISZ | 77 | |
| | C | | 93 | |
| | D | BBL | C0 | |
| | E | NOOP | | |
| | F | NOOP | | |
| | 0A0 | LDM | D5 | |
| | 1 | XCH | BA | |
| | 2 | JMS | 50 | |
| | 3 | | 56 | |
| | 4 | FIM | 24 | |
| | 5 | | 30 | |
| | 6 | JMS | 50 | |
| | 7 | | 6E | |
| | 8 | JMS | 50 | |
| | 9 | | 95 | |
| | A | FIM | 24 | |
| | B | | 00 | |
| | C | JMS | 50 | |
| PROM 1 | D | | 6E | |
| | E | FIM | 24 | |
| | F | | 30 | |
| | 0B0 | JMS | 50 | |
| | 1 | | 78 | |
| | 2 | FIM | 24 | |
| | 3 | | 18 | |
| | 4 | JMS | 50 | |
| | 5 | | A6 | |
| | 6 | FIM | 24 | |
| | 7 | | 18 | |
| | 8 | JMS | 50 | |
| | 9 | | 6E | |
| | A | JMS | 50 | |
| | B | | 95 | |
| | C | | 41 | |
| | D | | 3E | |
| | E | | | |
| | F | | | |

| Address | | Instruction | | Comments |
|---|---|---|---|---|
| PROM 2 | 000 | FIM | 24 | |
| | 1 | | 30 | |
| | 2 | JMS | 50 | |
| | 3 | | 78 | |
| | 4 | FIM | 24 | MPR From 30 to 38 |
| | 5 | | 38 | |
| | 6 | JMS | 50 | |
| | 7 | | 6E | |
| | 8 | FIM | 24 | |
| | 9 | | 00 | |
| | A | JMS | 50 | |
| | B | | 78 | |
| | C | FIM | 24 | MPCND From $0_0$ to $2_0$ |
| | D | | 20 | |
| | E | JMS | 50 | |
| | F | | 6E | |
| | 010 | LDM | D4 | Pass CTR = 8 |
| | 1 | XCH | BC | |
| | 2 | JMS | 50 | Clear IB |
| | 3 | | 66 | |
| | 4 | LDM | DF | |
| | 5 | XCH | BA | |
| | 6 | FIM | 26 | RS MPR 1 |
| | 7 | | 3F | |
| | 8 | JMS | 50 | |
| | 9 | | 58 | |

-continued

| Address | | Instruction | | Comments |
|---|---|---|---|---|
| | A | JCN | 12 | |
| | B | | 29 | |
| PROM 2 | C | JUN | 42 | |
| | D | | 30 | |
| | E | | 00 | |
| | F | | 00 | |
| | 020 | | 00 | Store Ans. Return |
| | 1 | | 00 | |
| | 2 | ISZ | 7C | |
| | 3 | | 14 | |
| | 4 | FIM | 24 | |
| | 5 | | 00 | |
| | 6 | JMS | 50 | |
| | 7 | | 6E | |
| | 8 | BBL | C0 | |
| | 9 | FIM | 24 | Add MPCND |
| | A | | 20 | |
| | B | JMS | 50 | |
| | C | | A6 | |
| | D | JU | 42 | |
| | E | | 1C | |
| | F | | | |
| | 030 | FIM | 24 | |
| | 1 | | 20 | |
| | 2 | LDM | D8 | |
| | 3 | XCH | BB | |
| | 4 | LDM | DF | |
| | 5 | XCH | BA | |
| | 6 | CLC | F1 | |
| | 7 | SRC | 25 | |
| | 8 | RDM | E9 | |
| PROM 2 | 9 | RAL | F5 | |
| | A | WRM | E0 | |
| | B | INC | 65 | |
| | C | ISZ | 7B | |
| | D | | 37 | |
| | E | JU | 42 | |
| | F | | 22 | |
| | 040 | FIM | 24 | $P_0 \rightarrow$ IB |
| | 1 | | 10 | |
| | 2 | JMS | 50 | |
| | 3 | | 78 | |
| | 4 | JMS | 50 | IB × 10 |
| | 5 | | 95 | |
| | 6 | | 00 | |
| | 7 | | 00 | |
| | 8 | | 00 | |
| | 9 | | 00 | |
| | A | FIM | 24 | IB to DVSR |
| | B | | 38 | |
| | C | JMS | 50 | |
| | D | | 6E | |
| | E | JMS | 50 | Clear IB |
| | F | | 66 | |
| | 050 | FIM | 24 | Clear QUOT |
| | 1 | | 20 | |
| | 2 | JMS | 50 | |
| | 3 | | 6E | |
| | 4 | FIM | 24 | PR − $P_0 \rightarrow$ IB |
| PROM 2 | 5 | | 30 | |
| | 6 | JMS | 50 | |
| | 7 | | 78 | |
| | 8 | LDM | D4 | Set Pointer |
| | 9 | XBC | BC | |
| | A | FIM | 24 | Sub |
| | B | | 38 | |
| | C | JMS | 51 | |
| | D | | 90 | |
| | E | LDM | DF | |
| | F | XCH | BA | |

-continued

TABLE GIVING PROGRAM LIST

| Address | | Instruction | | Comments |
|---|---|---|---|---|
| | 060 | JMS | 50 | |
| | 1 | | 4A | |
| | 2 | CMC | F3 | |
| | 3 | RAR | F6 | |
| | 4 | | 42 | |
| | 5 | | 86 | |
| | 6 | LDM | D8 | |
| | 7 | XCH | BA | |
| | 8 | FIM | 24 | |
| | 9 | | 20 | |
| | A | SRC | 25 | |
| | B | BDM | E9 | |
| | C | RAL | F5 | |
| | D | WDM | E0 | |
| | E | INC | 65 | |
| | F | ISZ | 7A | |
| | 070 | | 6A | |
| | 1 | ISZ | 7C | |
| PROM 2 | 2 | | 7C | |
| | 3 | FIM | 24 | |
| | 4 | | 20 | |
| | 5 | JMS | 50 | |
| | 6 | | 78 | |
| | 7 | FIM | 24 | |
| | 8 | | 30 | |
| | 9 | JMS | 50 | |
| | A | | 6E | |
| | B | BBL | C0 | |
| | C | XCH | BF | |
| | D | RAL | F5 | |
| | E | JCN | 12 | |
| | F | | 5A | |
| | 080 | FIM | 24 | |
| | 1 | | 38 | |
| | 2 | JMS | 50 | |
| | 3 | | A6 | |
| | 4 | JU | 42 | |
| | 5 | | 5E | |
| | 6 | | BF | |
| | 7 | | AF | |
| | 8 | | F5 | |
| | 9 | | 42 | |
| | A | | 66 | |
| | B | | | |
| | C | | | |
| | D | | | |
| | E | | | |
| | F | | | |
| PROM 2 | 090 | | | |
| | 1 | | | |
| | 2 | | | |
| | 3 | | | |
| | 4 | | | |
| | 5 | | | |
| | 6 | | | |
| | 7 | | | |
| | 8 | | | |
| | 9 | | | |
| | A | | | |
| | B | | | |
| | C | | | |
| | D | | | |
| | E | | | |
| | F | | | |

What is claimed is:

1. A system for measuring the flow of solids in a pneumatic conveying system having a conduit with an air inlet, a solids inlet, and a mixture outlet, the measuring system comprising:
   transducer means coupled to the conduit for responding to a pneumatic pressure developed therein to produce a pressure-representing signal;
   means for sequentially sampling the pressure-representing signal to provide at different times a reference-value-representing signal and an operating-value-representing signal, the sampling means providing the reference-value-representing signal when only air flows through the conduit, and providing the operating-value-representing signal at a time when both air and solids flow through the conduit;
   storage means for holding the reference-value-representing signal, the storage means providing the reference-value-representing signal it holds at the same time that the sampling means provides the operating-value-representing signal; and
   signal responsive means for determining the mass flow of solids on the basis of a linear function defined by first and second terms, the first term being proportional to the difference between the operating value and the reference value, and the second term being the reciprocal of the reference value.

2. A measuring system according to claim 1 and further comprising manually adjustable means for specifying a constant of proportionality for the first term.

3. A measuring system according to claim 2 wherein the sampling means provides for repetitiously sampling the pressure-representing signal so that the operating-value-signal repeatedly provides information as to instantaneous pressure, and further comprising means for accumulating a total to designate the amount of solids conveyed by the conveying system.

4. A measuring system according to claim 1 wherein the transducer means is adapted to respond to gage pressure, and wherein the measuring system includes a single tube coupling the conduit to the transducer means.

5. A measuring system according to claim 1 and further comprising manually adjustable means for specifying a constant of proportionality for the first term, and wherein the means for determining includes multiplying means for multiplying the specified constant of proportionality by said difference between the operating value and the reference value.

* * * * *

UNITED STATES PATENT AND TRADEMARK OFFICE
CERTIFICATE OF CORRECTION

PATENT NO. : 4,006,349

DATED : February 1, 1977

INVENTOR(S) : Mark William Royston

It is certified that error appears in the above-identified patent and that said Letters Patent are hereby corrected as shown below:

In the specification, Column 1, line 21, "scaing" should read -- scaling --; line 66, after "constant" delete "porportionally for"; line 66, after "proportionality" insert -- for the --. Column 2, line 39, "$P_1$" should read -- $P_a$ --; line 52, "$Q_1$" should read -- $Q_a$ --. Column 3, line 6, "the" should read -- these --; line 63, "th" should read -- the --. Column 4, line 51, "$P_1$" should read -- $P_a$ --. Column 7, line 2, "th" should read -- the --.

In the tables, Column 10, between lines 35 and 40, that portion of the table reading

| | | |
|---|---|---|
| ØDØ | ISZ | 7B |
| 1 | | 5B |
| 2 | ISZ | 7 |
| 3 | | 56 |
| 4 | BBL | C0 |

Part of Right Shift IB should read

| | | |
|---|---|---|
| ØDØ | ISZ | 7B |
| 1 | | 5B |
| 2 | ISZ | 7A |
| 3 | | 56 |
| 4 | BBL | CØ |

Part of Right Shift IB

UNITED STATES PATENT AND TRADEMARK OFFICE
CERTIFICATE OF CORRECTION

PATENT NO. : 4,006,349

DATED : February 1, 1977

INVENTOR(S) : Mark William Royston

It is certified that error appears in the above-identified patent and that said Letters Patent are hereby corrected as shown below:

between lines 50 and 60, that portion of the table reading

"
```
50
         Prom 0    2    JMS    50  ⎫
                   3           95  ⎬   IB × 10
                        JMS    50  ⎫
                   4           EC  ⎬   IB + F ⟶
                   5    LD     A9                   ⎫ Part of
55                      DAC    F8                   ⎬ Decimal
                   6    XCH    B9                   ⎭ Inputs
                   7    ISZ    7E
                   8           DC
                   9    BBL    C0
                   A
60                 B
```
"

should read

```
        PROM 0    2    JMS    50 ⎫
                  3           95 ⎬   IB × 10                              ⎫
                  4    JMS    50 ⎫                                        ⎬  Part of
                  5           EC ⎬   IB + F ➔ IB                          ⎬  Decimal
                  6    LD     A9                                          ⎬  Inputs
                  7    DAC    F8                                          ⎭
                  8    XCH    B9
                  9    ISZ    7E
                  A           DC
                  B    BBL    C0
```
--;

UNITED STATES PATENT AND TRADEMARK OFFICE
CERTIFICATE OF CORRECTION

PATENT NO. : 4,006,349

DATED : February 1, 1977

INVENTOR(S) : Mark William Royston

It is certified that error appears in the above-identified patent and that said Letters Patent are hereby corrected as shown below:

Column 11, between lines 55 and 60, that portion of the table reading

```
      F    FIM   24  ⎫
      F          30  ⎬  PR - P0  ⟶
     030   JMS   50  ⎭  Save PT - PA
      1          6E
                                            60
      2    JMS   52  ⎫  Divide R30 ÷ 10 × R10 ⟶ R30
      3          40  ⎭
``` should read

```
      E    FIM   24  ⎫
      F          3Ø  ⎬  PR - PØ ♦ 3Ø
     Ø3Ø   JMS   5Ø  ⎭  Save PT - PA
      1          6E
```

Signed and Sealed this second Day of August 1977

[SEAL]

Attest:

RUTH C. MASON
Attesting Officer

C. MARSHALL DANN
Commissioner of Patents and Trademarks